(12) United States Patent
Budgett et al.

(10) Patent No.: US 12,072,257 B2
(45) Date of Patent: *Aug. 27, 2024

(54) IMPLANTABLE PRESSURE SENSOR

(71) Applicant: Kitea Health Limited, Auckland (NZ)

(72) Inventors: David Mortimer Budgett, Auckland (NZ); Dixon Pok Chung Leung, Auckland (NZ); John Daniel McCormick, Auckland (NZ)

(73) Assignee: Kitea Health Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/864,484

(22) Filed: Jul. 14, 2022

(65) Prior Publication Data
US 2022/0341803 A1 Oct. 27, 2022

Related U.S. Application Data

(63) Continuation of application No. 16/462,216, filed as application No. PCT/IB2017/057194 on Nov. 17, 2017, now Pat. No. 11,422,051.

(30) Foreign Application Priority Data

Nov. 18, 2016 (NZ) ........................................ 726534

(51) Int. Cl.
*G01L 27/00* (2006.01)
*A61B 5/03* (2006.01)
*A61M 27/00* (2006.01)

(52) U.S. Cl.
CPC .............. *G01L 27/005* (2013.01); *A61B 5/03* (2013.01); *A61B 5/031* (2013.01); *A61M 27/00* (2013.01); *A61M 27/006* (2013.01); *G01L 27/00* (2013.01); *A61B 2562/0247* (2013.01)

(58) Field of Classification Search
CPC ......... G01L 27/005; G01L 27/00; A61B 5/03; A61B 5/031; A61B 2562/0247; A61B 2560/0223; A61M 27/00; A61M 27/006
See application file for complete search history.

(56) References Cited

U.S. PATENT DOCUMENTS

| | | | | |
|---|---|---|---|---|
| 3,601,128 | A * | 8/1971 | Hakim | A61M 25/00 604/9 |
| 11,422,051 | B2 * | 8/2022 | Budgett | A61M 27/006 |
| 2001/0027677 | A1 * | 10/2001 | Sgourakes | G01L 27/005 73/1.57 |
| 2016/0303318 | A1 | 10/2016 | Burke et al. | |

OTHER PUBLICATIONS

Second Office Action dated Jul. 13, 2022 from China National Intellectual Property Administration for CN Application No. 201780082938.4.

* cited by examiner

*Primary Examiner* — Peter J Macchiarolo
*Assistant Examiner* — Anthony W Megna Fuentes
(74) *Attorney, Agent, or Firm* — JCIP; Joseph G. Chu; Jeremy I. Maynard

(57) ABSTRACT

A device for use in pressure sensing has a housing enclosing a chamber and having at least one port that communicates with the chamber. A pressure sensor receives fluid pressure from the chamber. The chamber has a compliance that exhibits a marked change in volumetric stiffness repeatably at a fixed pressure.

20 Claims, 14 Drawing Sheets

IMPLANTABLE PRESSURE SENSOR

CROSS REFERENCE TO RELATED APPLICATIONS

The present application is a continuation application of U.S. patent application Ser. No. 16/462,216 having a filing date of May 18, 2019, which is a U.S. national phase of PCT Application No. PCT/IB2017/057194 having a filing date of Nov. 17, 2017, which claims foreign priority to NZ Application No. 726534 having a filing date of Nov. 18, 2016, the contents of each are hereby incorporated by reference in their entireties.

FIELD OF THE INVENTION

The present invention relates to pressure sensors, particularly to pressure sensors for implanting on a long term basis.

SUMMARY OF THE PRIOR ART

Implanted pressure sensors are known for use as a stand alone device, or as part of a larger device. One particular issue with implanted sensors is to maintain an accurate output. Sensors typically are either relative pressure sensors, or absolute pressure sensors. Relative pressure sensors work with a reference pressure that can be applied from outside the body. Absolute pressure sensors are self-contained, and include a sealed reference pressure chamber. Usually the absolute pressure sensor reference chamber is evacuated, to minimize the impact of variation in temperature, but another known reference pressure may be provided where either the temperature will be stable in use, or a temperature sensor is included in the system which can be used to adjust pressure readings from the sensor.

A relative pressure sensor has a pathway for externally applying a reference pressure. This is usually a catheter or tube connecting to the sensor and extending from the body of the user. This makes the sensor unsuitable for long term use, or use outside the clinical environment.

Absolute pressure sensors are known to have problems with the sensor output drifting over time. They are susceptible to gradual changes in the response of the mechanical components over time, and to changes in the response of the electrical components over time. They are also susceptible to accumulation of deposits on and within components and housings. This drift is not significant where sensors are used for short periods, but may become significant where sensors are implanted and long term use is desired.

SUMMARY OF THE INVENTION

It is an object of at least one embodiment of the present invention to provide a sensor which goes some way to overcoming the above disadvantages or which will at least provide the health sector with a useful choice.

In a first aspect the present invention may broadly be said to be a device comprising:

a housing enclosing a chamber and having at least one port that communicates with the chamber, a pressure sensor receiving fluid pressure from the chamber, the chamber having a compliance that exhibits a marked change in volumetric stiffness repeatably at a fixed pressure.

Preferably the device includes a flexible wall portion forming part of a wall of the chamber, a sealed cavity divided from the chamber by the flexible wall portion, such that an increasing pressure in the chamber causes increasing deflection of the flexible wall portion, the sealed cavity or housing being shaped such that as the pressure in the chamber transitions through a first pressure part of the wall portion transitions from being in contact with a structure of the cavity or housing to being out of contact with the structure.

Preferably the flexible wall portion comprises a thin diaphragm and portions of the diaphragm can continue to deflect at pressures above and below the contact pressure.

Preferably the flexible wall portion is out of contact with the structure at pressures below the first pressure, and in contact with the structure at pressures above the first pressure.

Preferably there is no additional detector for determining contact of the flexible wall portion with the housing or cavity.

Preferably the pressure sensor is located in the housing.

Preferably the pressure sensor is within an enclosure sealed from the chamber by a flexible membrane, the enclosure being filled with an incompressible liquid.

Preferably at least one port includes connection for flexible tubing.

Preferably the housing includes an inlet port and an outlet port and both inlet and outlet ports include connection for flexible tubing.

Preferably the device includes an interface from the pressure sensor to a controller.

Preferably the device includes a controller connected to the pressure sensor, an external communications interface connected with the controller and a power supply connected to supply power to the controller.

In another aspect the present invention may be said to broadly consist in an assembly comprising a device as hereinbefore described having a first flexible tube extending from the inlet port and a second flexible tube extending from the outlet port.

In another aspect the present invention may be said to broadly consist in a hydrocephalus shunt comprising an assembly as hereinbefore described and a shunt valve connected with the flexible tube extending from the outlet port.

In another aspect the present invention may be said to broadly consist in a system including a device as hereinbefore described including a processor programmed to process data from the pressure sensor in a calibration method comprising identifying a pressure data point from the pressure sensor that corresponds with a time when the compliance of the chamber changes.

Preferably the program identifies the time when the compliance of the chamber changes by identifying a knee feature in a pressure data series recorded over the duration of a calibration event.

Preferably the program identifies a knee feature according to distinct changes in gradient of pressure over time.

Preferably the program sets a zero offset for use in relation to the pressure sensor based on the recorded output of the pressure at the identified time.

Preferably the program sets a zero offset for use in relation to the pressure sensor based on the result of multiple instances of the calibration method.

Preferably the program compares the results of multiple instances of the calibration method and discards at least some of the results in calculating a new zero offset for the pressure sensor.

Preferably the processor may be any one or more of a microprocessor or an FPGA device array or complex instruction set computing (CISC) microprocessor, reduced instruction set computer (RISC) microprocessor or an ASIC device or digital signal processor or a CPU or a desktop computer or laptop or a smartphone or tablet or a cloud based processor or a cloud server.

In another aspect the present invention may be said to broadly consist in a recalibration method comprising the steps of occluding flexible tubes connected to ports of a housing of a pressure sensor, moving one of the occlusions toward the housing Preferably the occlusion is moved steadily toward the housing.

Preferably the diaphragm within the pressure sensor deflects in correspondence to the increasing pressure within a chamber within the housing, compensating for the loss of volume within a tube due to the movement of the occlusion.

Preferably the pressure sensor is configured to read the pressure in the chamber.

Preferably a discontinuity or change in the pressure rate is detected and the discontinuity is used to recalibrate the value of the pressure sensor output based on the detected discontinuity value.

Preferably the discontinuity value is used as an offset or bias value to recalibrate the output of the pressure sensor.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

DESCRIPTION OF THE DRAWINGS

A pressure sensor will be described with reference to the accompanying drawings.

DETAILED DESCRIPTION OF THE INVENTION

The present invention relates to pressure sensors, particularly for implanting in the body. The sensor is intended for long term use, for example for periods of at least months, or multiple years.

The sensor is intended for use in persons wishing the option of residing outside the clinical environment, and who wish to go about their usual activity.

For example the sensor may be used in persons having hydrocephalus. This condition involves potential for excessive accumulation of cerebrospinal fluid within the ventricles of the brain. The disorder affects both adults and children and is lifelong. This condition can be managed with a hydrocephalus shunt. However shunt failure due to blockage is common. The condition, or monitoring for correct operation of any implanted shunt, or both, could be better managed with reliable long term intracranial pressure monitoring.

Figure 3:
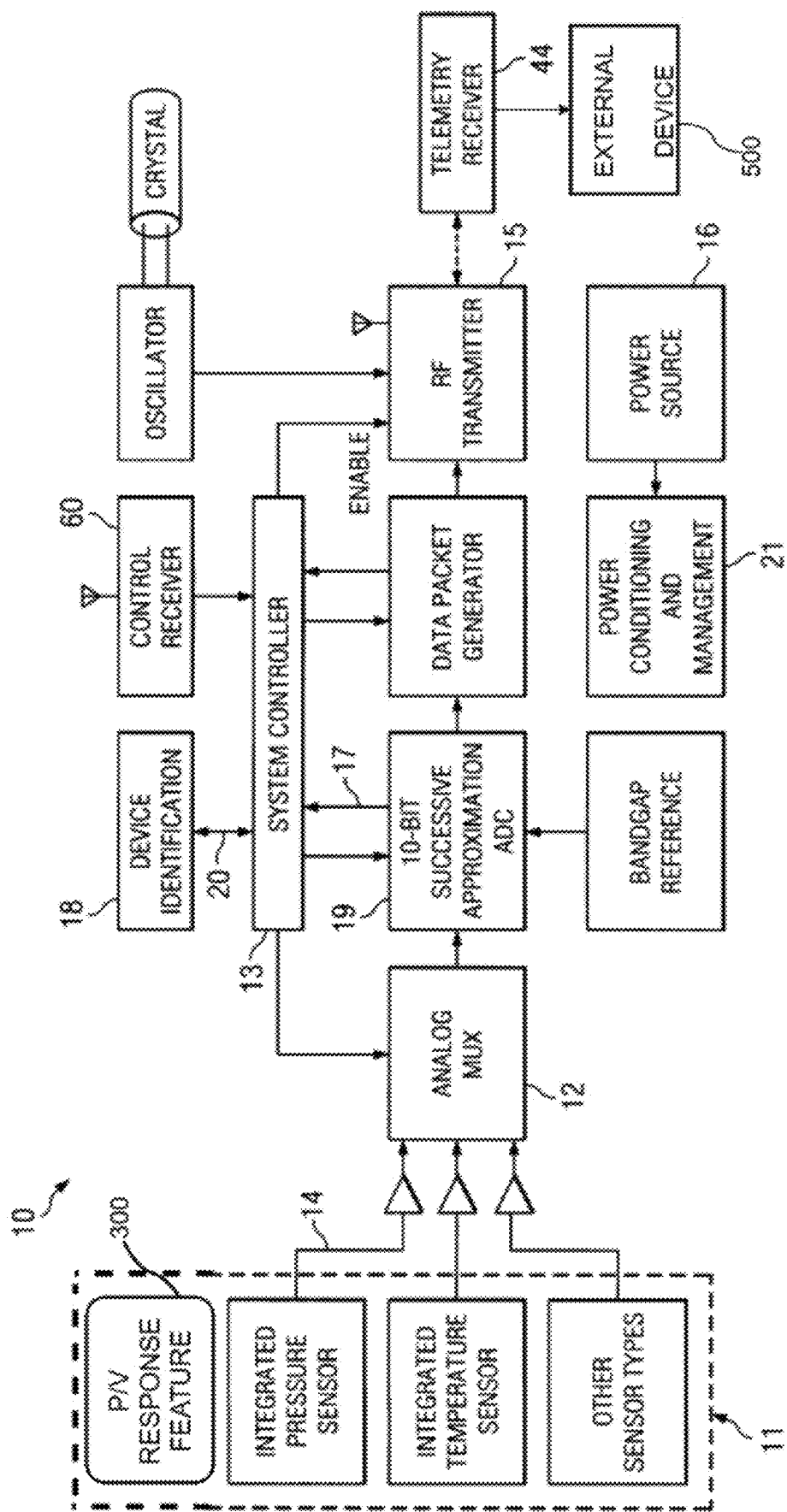
FIG. 3 is a schematic diagram illustrating the main parts of a device including housing, displacer, sensor, processor and communications interface.

Example devices are known in the prior art for this purpose. For example implantable devices which include an absolute pressure sensor, processor and communication interface are described in U.S. Pat. No. 6,533,733 with particular reference to FIGS. 3 and 4, and U.S. Pat. No. 6,248,080 with particular reference to FIG. 1c, the relevant disclosures of which are hereby incorporated in their entirety.

The present invention suggests adaptation of the sensor component of such systems to provide a characteristic output curve (plotting sensor output against applied pressure) including a recognizable artefact that reliably occurs at a pressure, and adaptation of the program executed by the processor of the device to include a calibration function that recognizes the presence of this artefact.

For example, in a device constructed according to U.S. Pat. No. 6,248,080 the pressure sensor module 20 would include features to create the characteristic curve including recognizable artefact, and the program with recalibration function would be executed in microprocessor 120. Alternatively the program with recalibration function could be executed in an external device (eg: device 500 in FIG. 3), in communication with the implanted device, based on sensor data collected by the implanted device. The external device could be any suitable computing device whether in close proximity to the implanted device or communicating over a network such as the Internet.

Figure 1:
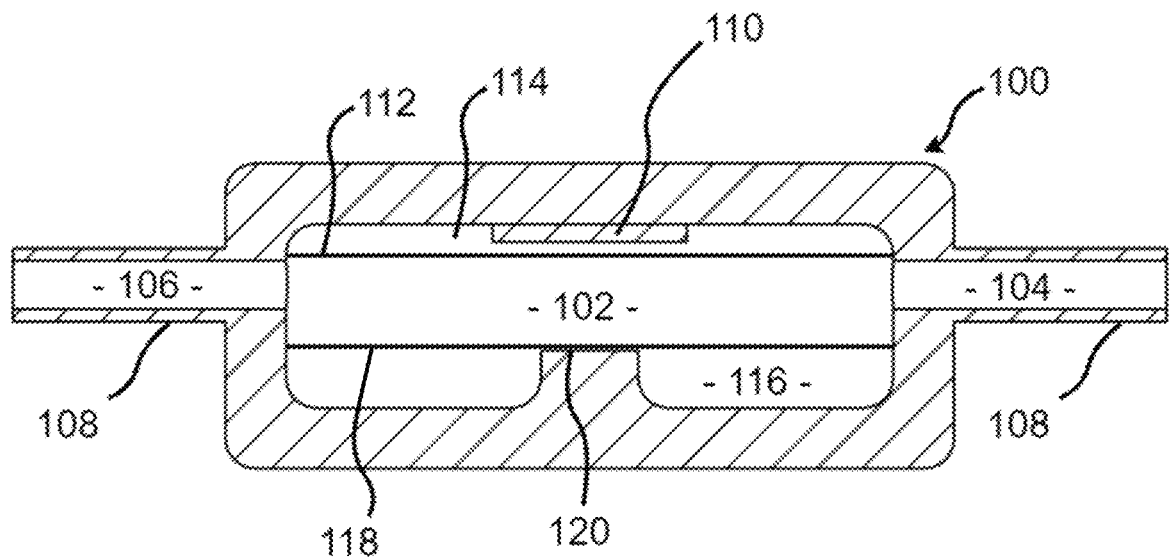
FIG. 1 is a cross section through a pressure sensor housing according to one sensor embodiment.

Referring to FIG. 1, one aspect of the invention comprises a sensor component. The sensor component includes a housing 100. The housing 100 includes an internal chamber 102. The housing 100 includes an inlet 104 to the chamber 102 and an outlet 106 from the chamber 102. Outlet port 106 is optional. An outlet port is not necessary for the pressure sensing or calibration, but may be useful if the device is used as part of a hydrocephalous shunt. The inlet and outlet may be essentially identical, and the role of either port is not important. The housing may be formed with any suitable connection or connector 108 at the inlet port, the outlet port or both.

A pressure sensor 110 of the absolute type, for example a MEMS sensor, is located in the housing. The pressure sensor 110 is located in the housing in pressure communication with the chamber. The pressure sensor 110 is preferably located in a secondary space divided from the chamber by a membrane 112 in a cavity 114 defined by the housing and membrane. The cavity 114 is preferably filled with a substantially incompressible liquid such as an oil. Pressure in the cavity is transferred to the sensor 110 through the oil.

A second cavity 116 is divided from the chamber 102 by a diaphragm 118. This cavity is sealed and contains a gas or vacuum. Preferably this cavity contains a vacuum. A vacuum is temperature independent. Alternatively, the cavity may contain a gas at a known pressure. In this case the volumetric response will also be a function of temperature. The temperature can be measured by many MEMS pressure sensors such as the LPS22HBTR from ST Microelectronics. The diaphragm 118 may deflect according to the relative pressure between the cavity 116 and the chamber 102, thereby changing the volume of the chamber 102 according to the fluid pressure in the chamber 102. For example, as the pressure in chamber 102 rises from a first pressure to a second pressure, the diaphragm deflects to progressively reduce the size of the cavity 116 and increase the size of the chamber 102.

The cavity 116 and diaphragm 118 are formed so that there is a discernible characteristic in the change in volume relative to change in pressure that occurs at a fixed relative pressure between the chamber 102 and the cavity 116. In an embodiment this results from an abrupt increase in the effective stiffness of the diaphragm due to interaction between the diaphragm and an internal surface of the cavity 116. For example, in the illustrated embodiment, the surface of the cavity includes an upstand 120. As the relative pressure increases, the centre portion of the diaphragm eventually rests on the upstand 120. The annular portion of the diaphragm around the upstand 120 continues to deflect, but the effective stiffness of the diaphragm has been increased by supporting the centre location.

According to other embodiments the cavity may include a second upstand that will contact the annular portion of the diaphragm at a second pressure higher than the pressure causing the centre of the diaphragm to rest on the upstand 120. When the diaphragm is resting on both upstands, the diaphragm is still able to deflect but is now in a third state of effective stiffness.

According to further embodiments, the contact pressure of the diaphragm and the structure could be lower than the typical expected pressure, so that the diaphragm and structure are usually in contact, and come out of contact by pressure reduction in the calibration process. Later an example is given where a pinch process is performed to vary the pressure in the chamber, subsequently moving the pinch point in one direction will increase the pressure in the chamber, while moving the pinch point in the other direction will reduce the pressure in the chamber. In this example the pinch and roll process the roll would to increase the size of the occluded space.

According to further embodiments, the contact structure could be provided in the chamber and contact the chamber side of the diaphragm, rather than the cavity side. In still further embodiments, contacting structure could be provided on both sides, to contact at different chamber pressures.

Figure 6:
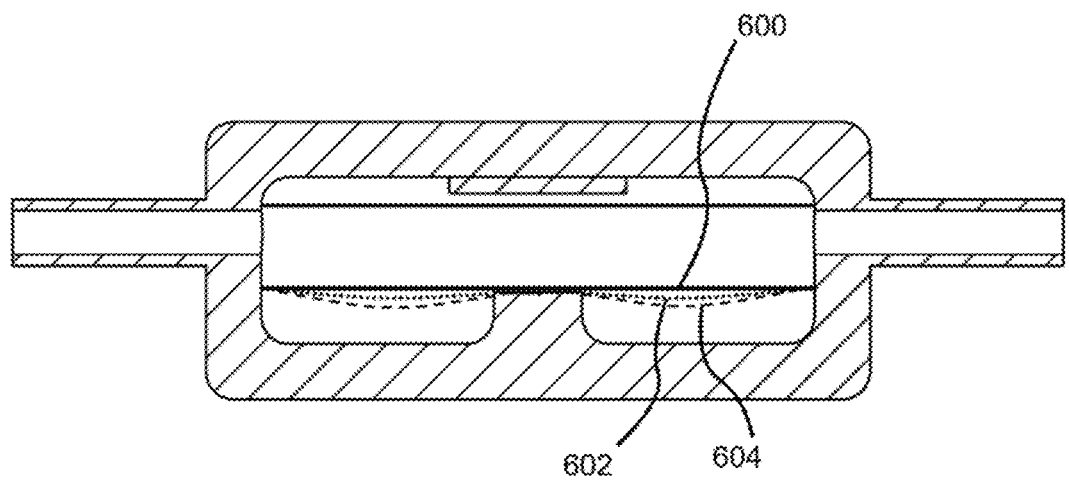
FIG. 6 is a cross section of part of the transducer of FIG. 1 illustrating, in an exaggerated form, deflections of the diaphragm at different moments in the graph of FIG. 5.

This is illustrated in FIG. 6, where the diaphragm is shown in a first, undeflected position 600 and a second position 602 (dashed line) when it has deflected sufficiently to contact the upstand 120. The diaphragm is shown in a third condition 604 (dotted line), where the surrounding portion of the diaphragm has continued to deflect under further increasing pressure.

The housing may be largely constructed from a stiff biocompatible material. For example the housing may be constructed largely from titanium. The pressure sensor may include integrated electronics and communicates through the wall of the housing, so the housing may include a radio frequency transparent window, or the housing, or a portion of the housing, may be formed from a ceramic such as alumina/zirconia/borosilicate glass, or a polymer.

The secondary space in which the sensor is located is filled with a pressure transmitting liquid, such as a silicone oil. This space is separated from the chamber by a membrane sufficiently flexible to minimize the damping of transmitted pressure. For example this may be a titanium membrane with a thickness less than 25 micrometres.

The housing surrounding the cavity may also be constructed from a stiff biocompatible material. For example this portion of the housing may be constructed from titanium. The upstand may be integral with the housing or may be a separate component secured in place, for example by adhesive.

The diaphragm may be a titanium membrane. Preferably the housing is also titanium such that the cavity may be hermetically sealed by welding the diaphragm to the housing, for example by laser welding. The cavity may be filled with an inert gas such as for example helium. Other inert gases may also be used to fill the cavity. The housing ports may be formed with the housing, for example from titanium. The ports preferably are adapted for connection of tubing such as medical grade silicone tubing.

Figure 7:
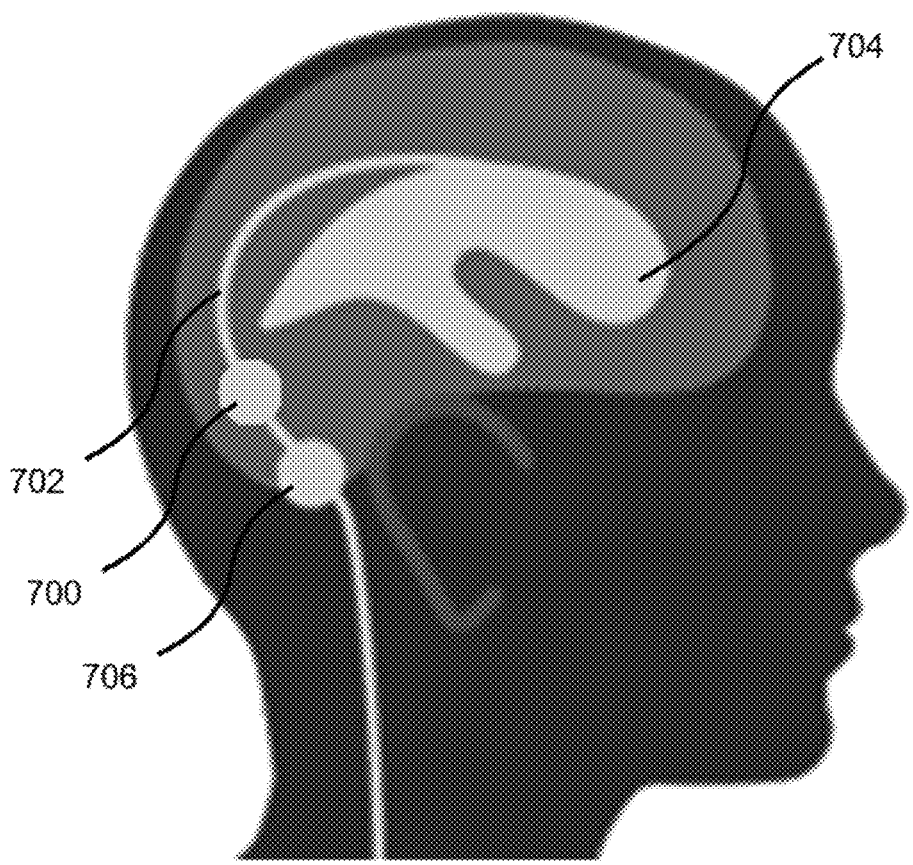
FIG. 7 is a sketch illustrating location of the sensor device in use.

As an implantable device the sensor component may be constructed to a size suitable to the particular purpose. For example for use in a hydrocephalus shunt, the sensor housing may be located subcutaneous, under the scalp of the patient, to one side of or to the back of the head—such as indicated in FIG. 7. In this location the device may be a substantial size, for example with an overall diameter of 10-15 mm and an overall thickness of 4-7 mm.

Where this component is included in a system, such as the hydrocephalus shunt of FIG. 7, the characteristic volumetric response to changing pressure in the chamber 102 can be used to recalibrate the pressure sensor 110. In such a system the sensor component 700 is located in series in a drainage tube 702 that extends from the ventricles 704 of the brain, preferably above a shunt valve 706 which can open or close the drainage tube according to a pressure condition in the brain. Accurate pressure readings in the shunt tube near the shunt valve are beneficial to determining whether the shunt valve is operating correctly.

Figure 5:
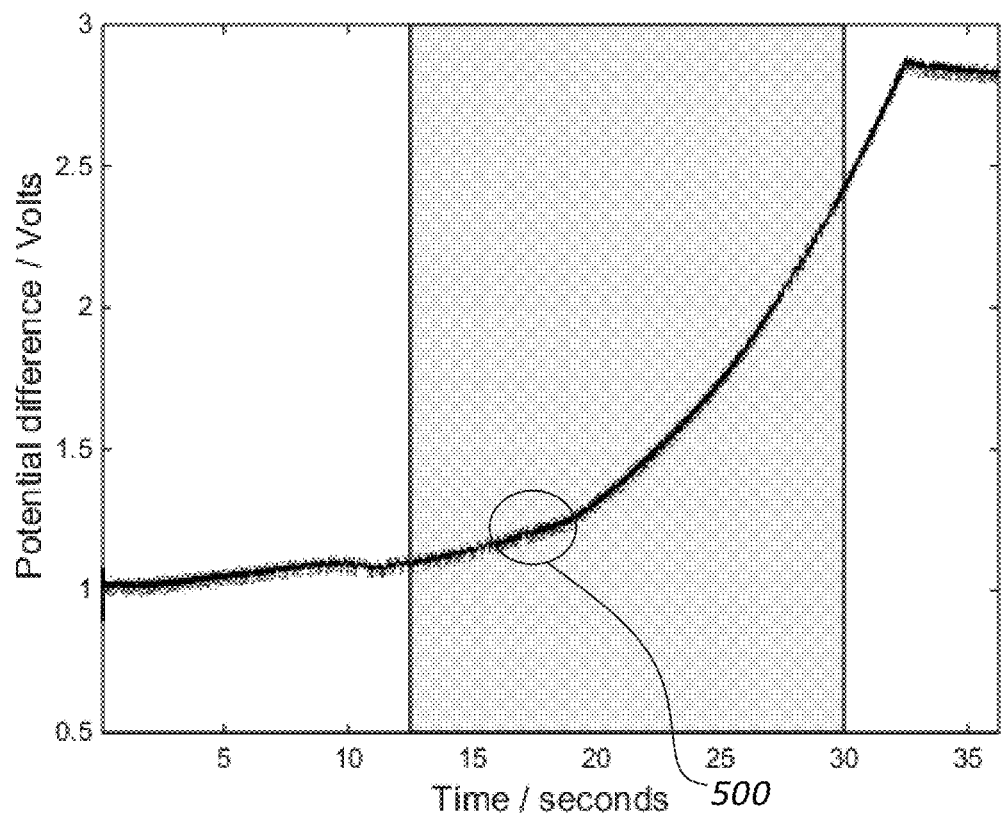
FIG. 5 is a graph plotting transducer output against time in a test sequence with a linearly increasing applied pressure.
Figure 8:
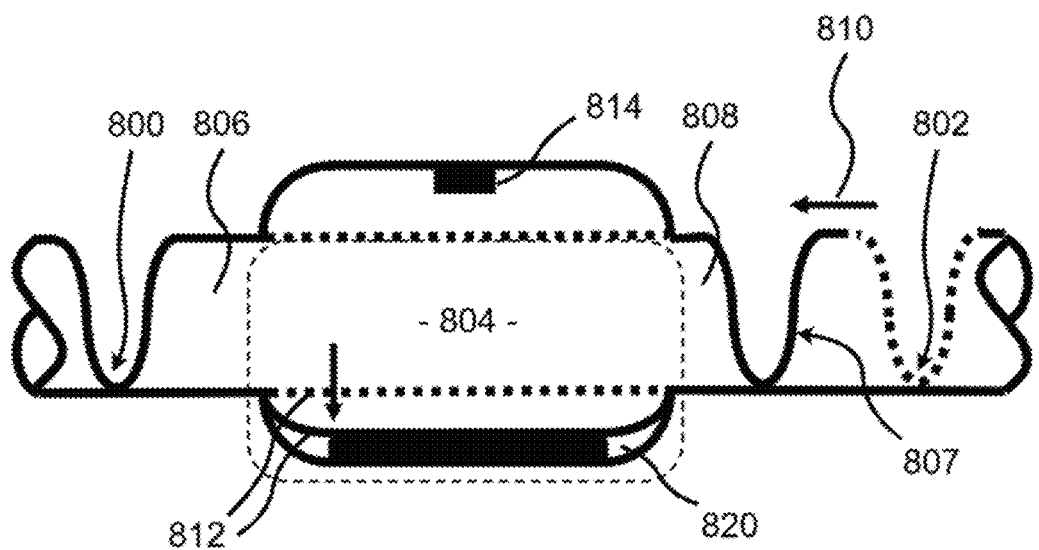
FIG. 8 is a diagram showing how a system including the sensor device may be physically manipulated in performing a calibration.
Figure 9:
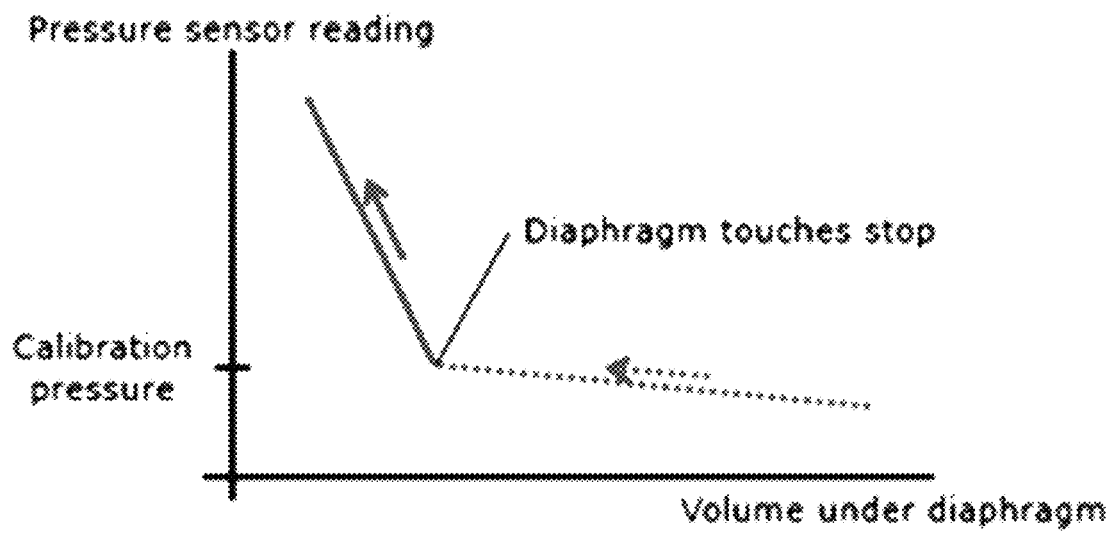
FIG. 9 is a graph relating the pressure in the chamber of the housing to the pressure in the housing when performing the calibration of FIG. 8.

For example, with reference to FIG. 8, a recalibration method may include pinching or otherwise occluding flexible tubes connected to the ports of the housing, as at locations 800 and 802. This defines an essentially sealed volume, including the chamber 804 and the portions of connected tube 806 and 808, containing a largely incompressible fluid (such as bodily liquids). One of the occlusions is then moved steadily toward the housing, as illustrated by occlusion 807 and by arrow 810, thereby progressively reducing the amount of tube 808 included in this sealed volume. The diaphragm 812 deflects in sympathy with the increasing pressure in the chamber 804, compensating for the loss of volume in the tube 808 by increasing the volume in the chamber. The sensor 814 reads the pressure in the chamber 804 while this is happening. A steady rate of movement of the pinch 802 leads to a steady rate of compensation by deflection of the diaphragm 812. A plot of the pressure that is induced in the chamber 804 to force this deflection depends on the stiffness of the diaphragm. At a fixed pressure this stiffness increases due to contact between the diaphragm and the upstand, and there is a substantial change in the rate at which the pressure in the chamber increases due to further reduction in volume of the tube. This is exemplified by the graph in FIG. 9, which plots the pressure in the chamber 804 against the volume in the cavity 820. A plot of pressure measured by the sensor 814 against time for such a calibration process will display a discernable discontinuity. An example plot is provided in FIG. 5. There is a discernible discontinuity in the gradient at location 500.

The output of the sensor can be processed to identify such a discontinuity, and the sensor system can be recalibrated on the assumption that this discontinuity occurred at the known fixed pressure.

An implanted system may include processing and communication facilities. Such a system is exemplified in FIG. 3.

This implanted system includes a sensor component 11, with one or more internal sensors, including a pressure sensor, with the sensing chamber characterized by a feature 300 (for example according to manner described above) to have a compliance to increasing pressure which exhibits a discernible artefact. The sensors provide data to a processing device. The processing device may include a controller 13 receiving data from the sensors via an interface 13. The controller 13 can communicate with external devices via a communication interface 15. The system is powered from a power supply including power source 16 and power conditioning 21. Such a processing device is described more completely in U.S. Pat. No. 6,533,733 which is hereby incorporated by reference.

In such a system there will have been an initial calibration of the sensor prior to implant. In addition, with the sensor component described above, there may be an initial calibration process to determine the chamber pressure at which the chamber compliance exhibits the characteristic change. This pressure is stored as a reference pressure for future calibration events.

Processing of signals from the sensor to identify calibration opportunities and to make recalibration steps may be completed by the processing device, by an external device, or by some combination of devices. Accordingly, the methods that will now be described could be implemented in software of the implantable system, software of external devices in direct or indirect communication with the implantable system, or distributed across some combination of devices.

Figure 4A:
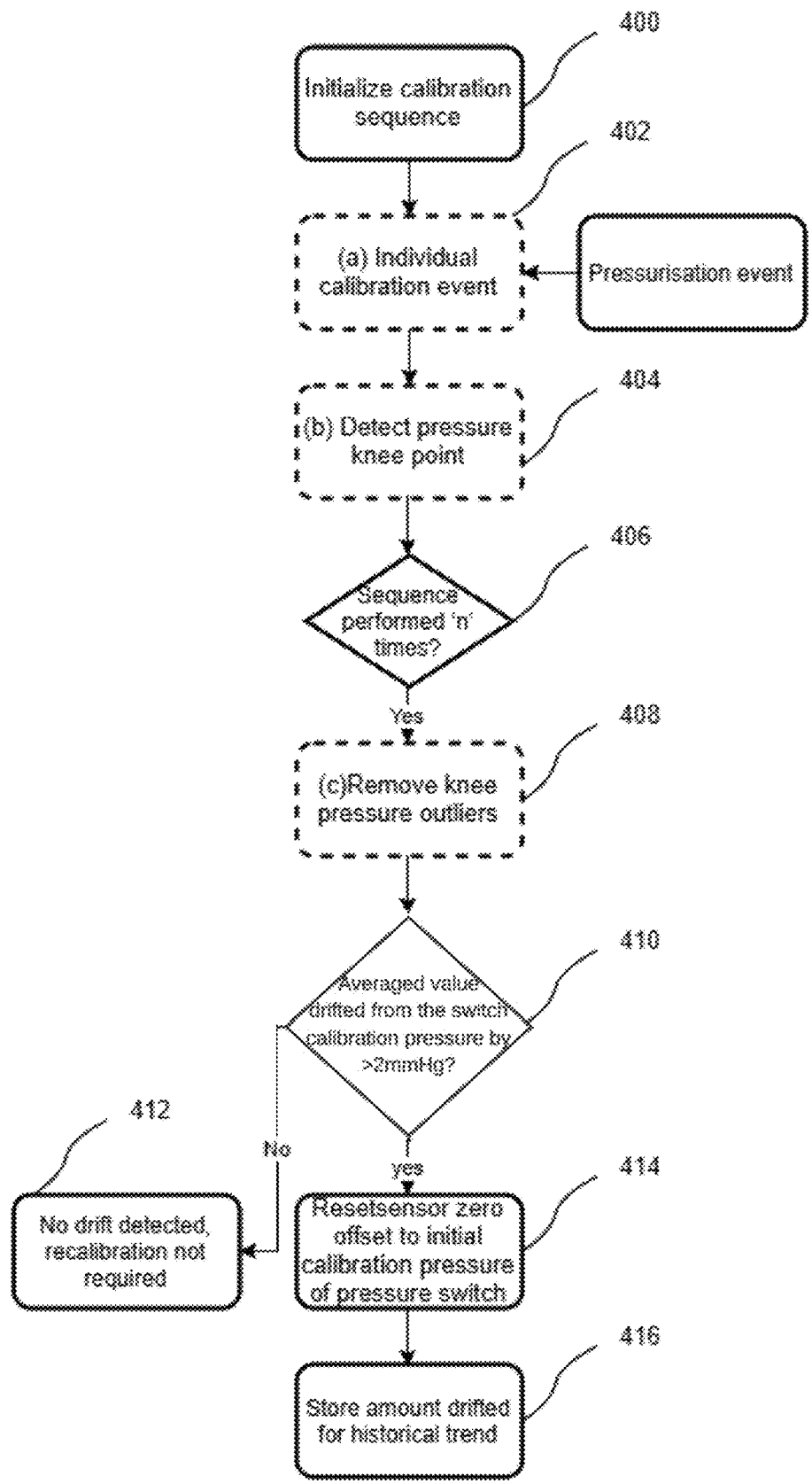
FIGS. 4a to 4d are charts outlining the operation of the processor in taking a sensor readings and in calibrating the sensor.
Figure 4B:
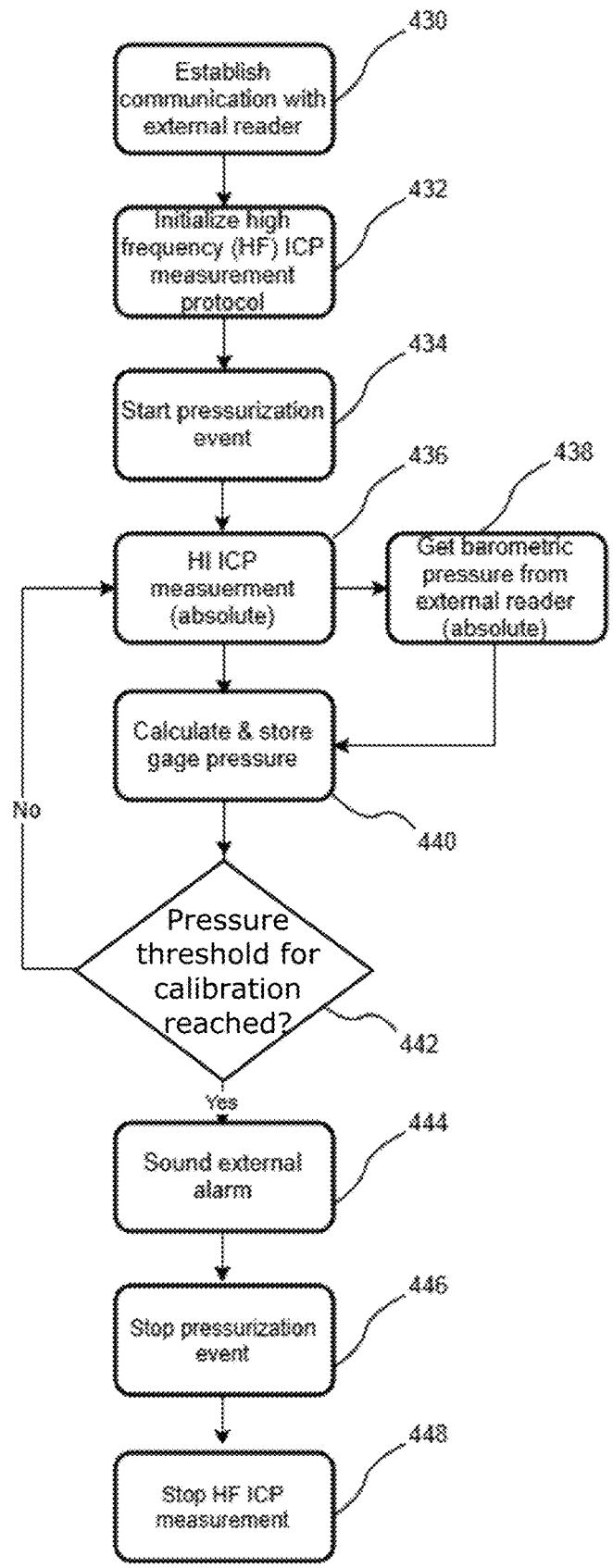
Figure 4C:
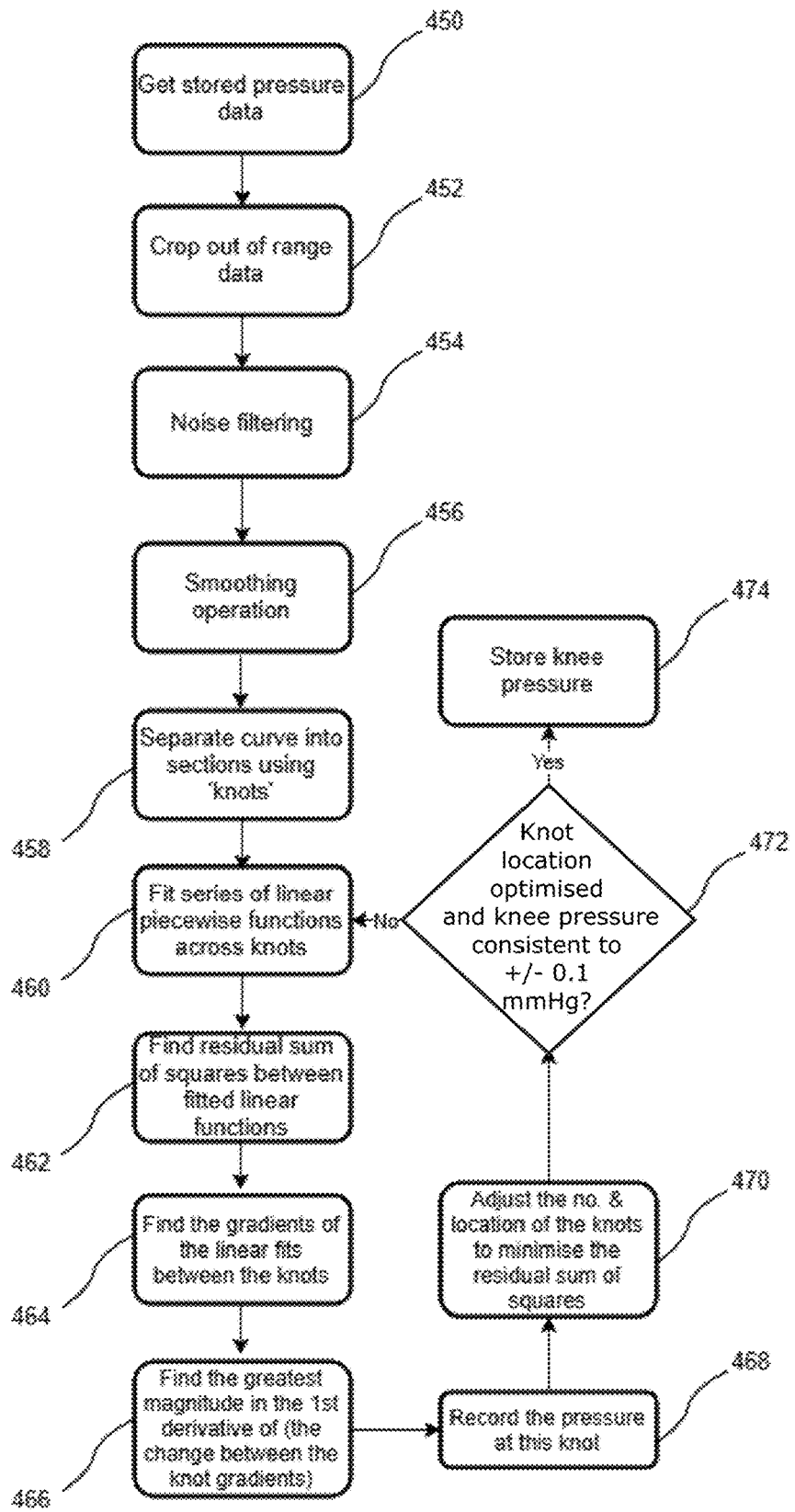

An example recalibration process is illustrated in FIGS. 4a to 4d. FIG. 4a provides an overall process, and FIGS. 4b to 4c provide additional detail in relation to certain steps in the overall process. The recalibration process is intended to be performed intermittently, with the controller usually devoted to the activity of monitoring the sensor output.

The calibration process commences at step 400 with initialization. Where this process is being run in the implantable device this may be in response to a command received from an external device.

The process proceeds to step 402, to perform an individual calibration event. This is detailed in FIG. 4a, and proceeds in parallel with external influence in the form of artificial elevation of the pressure. Step 402 produces a pressure dataset covering the period of a calibration event. At step 404 the process analyses the pressure dataset to identify a characteristic feature and a sensed pressure (knee pressure) at which this feature occurred. This step is detailed in FIG. 4b. The output of this step is the knee pressure at which a feature is determined to have occurred. Step 406 loops back to perform steps 402 and 404 a number ("n") times, so that actual recalibration can occur based on multiple pressurization events to enhance accuracy and reliability. Once sufficient repetitions have been made the process proceeds to discard outliers at step 408. This is detailed in FIG. 4d.

The process then proceeds to step 410 to decide whether to recalibrate. In particular the process compares the averaged knee pressure when the events occurred against a reference value based on the present calibration of the sensor to determine an amount of drift since the last recalibration. This amount of drift is compared with a threshold. If the drift is less than the threshold then the process proceeds to step 412 and no revision is made to the reference value and the process ends. If the drift is more than the threshold, then the process proceeds to step 414. The threshold may be set at a level according to what would be clinically significant. For example for cerebral pressure monitoring the threshold might be set as 2 mmHg or to some other value.

At step 414 the zero offset of the sensor is reset according to the drift determined at step 410, or according to the difference between the knee pressure determined at step 408 and in initial knee pressure stored at an initial calibration of the device.

The process preferably also stores the determined drift at step 416 for use in later analysis of sensor performance over time.

Step 402 is exemplified in greater detail with reference to FIG. 4b. At step 430 the implanted device communicates with an external device to establish the start of a calibration event. The external device preferably includes a barometric pressure sensor, or can obtain data from a barometric pressure sensor.

At step 432 the process commences high frequency pressure sensing, expecting a calibration process that occurs over a period of seconds or minutes. This differs from the typical monitoring conducted by the implanted device which may sample pressure on a much longer time scale, perhaps taking a sensor reading only each hour. The higher frequency pressure sensing may involve taking readings each second, or multiple times per second such as 20 readings per second or more. The selected frequency will depend on the intended calibration technique. The frequency must provide sufficient data for subsequent analysis to reliably determine a knee in the pressure versus time curve.

At step 434 a user is prompted to start a pressurization event. For example, in the case of a pinch/roll calibration process, the user may press closed the tube at either side of the pressure sense component, and then begin a roll of one finger toward the pressure sense component.

At steps 436 to 442 the process senses, calculates and stores pressure data until a threshold pressure is reached. The threshold pressure is substantially above the expected knee pressure, but below a pressure that might damage the sense component or connections. In the loop, at step 436 the pressure is read from the pressure sensor. A barometric pressure is read, preferably simultaneously, as at step 438, from an external barometric pressure sensor. The difference between the absolute sensed pressure and the barometric pressure is calculated and stored at step 440, along with the time of the reading, or as part of a known timed sequence of readings. At step 442 the process determines whether the threshold has been met, returning to step 436 of the threshold has not been met.

Once the pressure threshold has been reached at step 442, the process provides user feedback at step 444, preferably in the form of an audible or visual alarm. This alerts the user to stop the process that is providing the increasing pressure, as at step 446. This event measurement process then terminates at step 448 by stopping pressure measurement.

An example process for determining the presence of an artefact in the pressure profile generated in a calibration event is set out in FIG. 4c. This commences at step 450 by retrieving the data stored for a pressure calibration event, such as in the process of FIG. 4b. This dataset will include a time series of gage pressures.

Figure 10A:
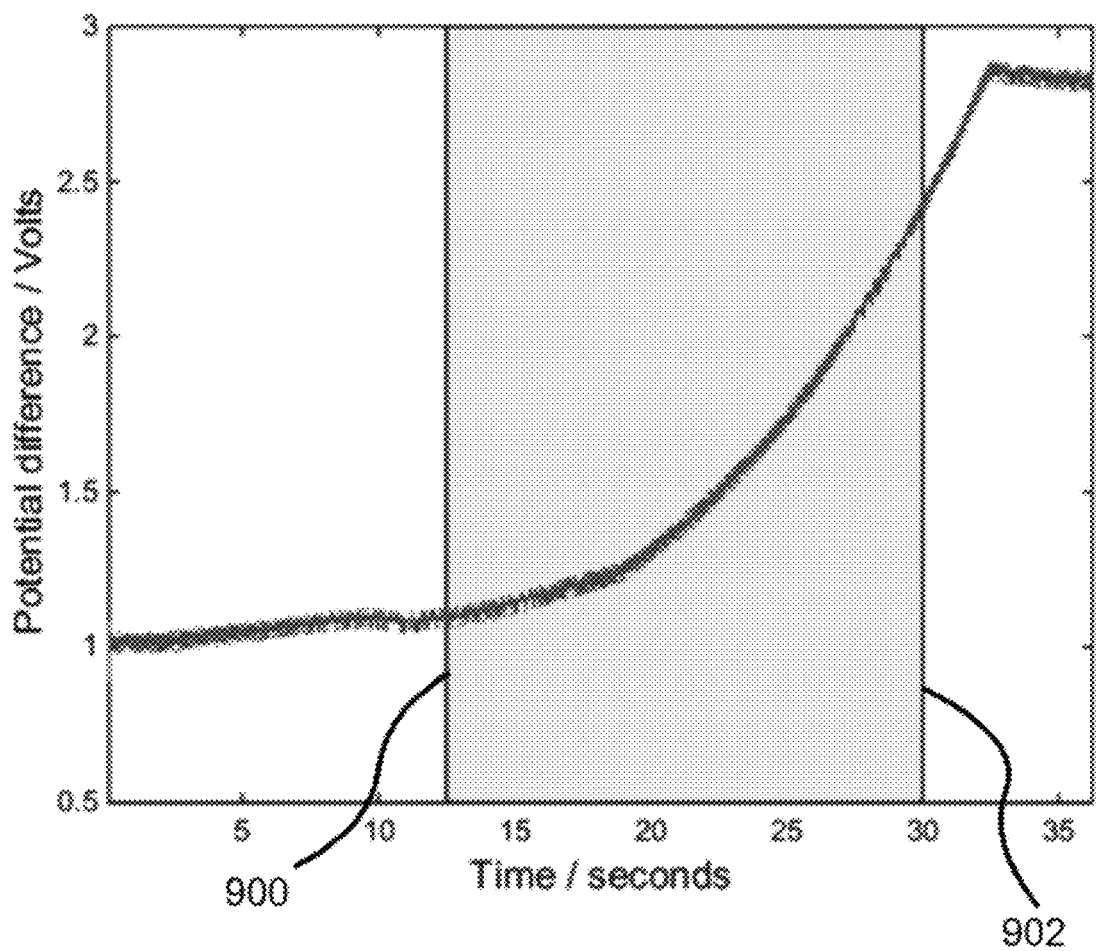
FIGS. 10a to 10f are a series of graphs that illustrate processing of sensor data to recognize a characteristic.

At step 452 the process may crop data that is out of range. For example the process may crop one or other end of the dataset or both to include entries that cover a time period when the pressure is continuously increasing from a threshold below an expected knee pressure to a threshold above an expected knee pressure. This range is preferably chosen sufficiently large to definitely include the knee pressure, and to sufficient data either side of the knee pressure to establish derivatives of fitted curves of the data on either side of the expect knee pressure. This is illustrated on an example dataset in FIG. 10a where data outside the region of interest defined by lower bound 900 and upper bound 902 is cropped, leaving a dataset covering only 17.5 seconds. Again 10a shows a plurality of data points about a line of best fit, the data points being shown as multiple dots or points on the graph.

Figure 10B:
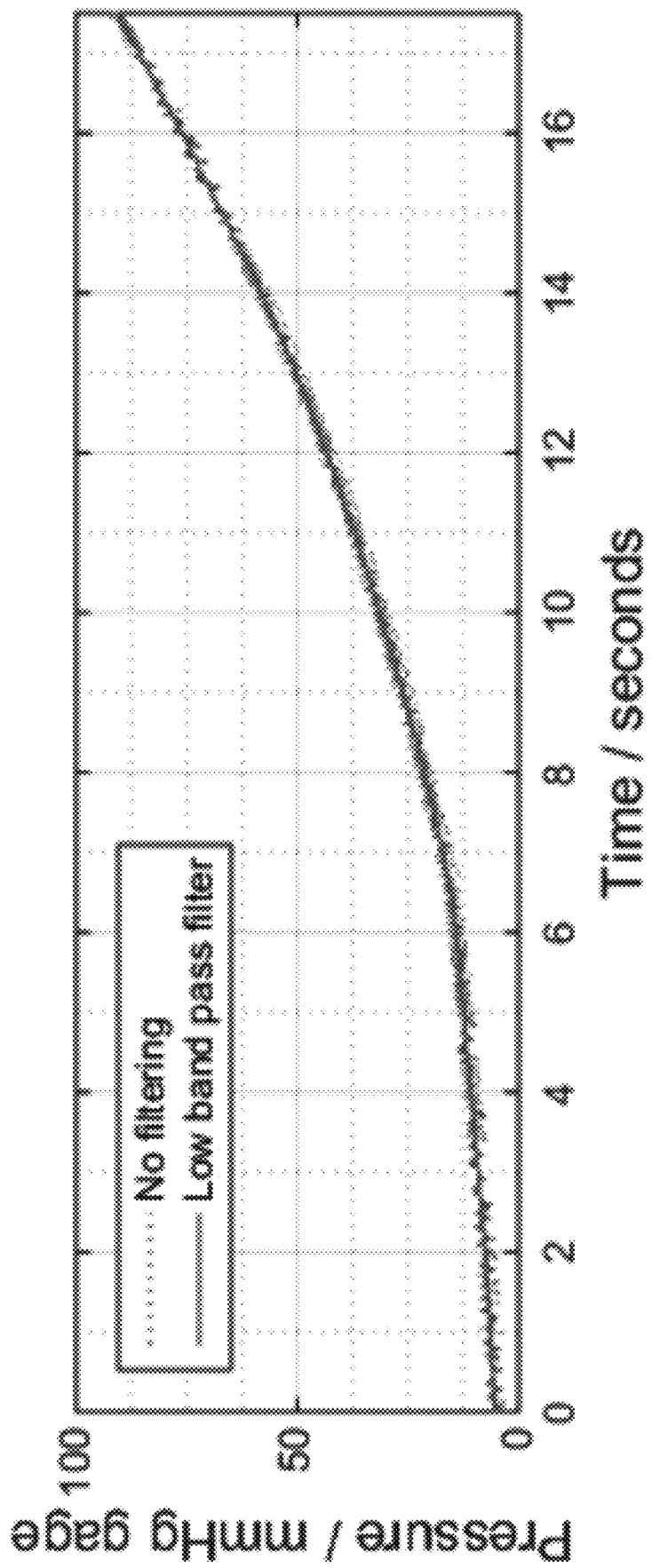

At step 454 the process filters the data set, for example using a low pass filter, as a first smoothing stage. This is illustrated in FIG. 10b in relation to the example cropped dataset from FIG. 10a. In FIG. 10b there are a plurality of dots or data points about the line that represent the unfiltered data points. The line is a low band pass filter applied to the data points i.e. like a line of best fit. The noise being filtered out produces a smoother curve.

Figure 10C:
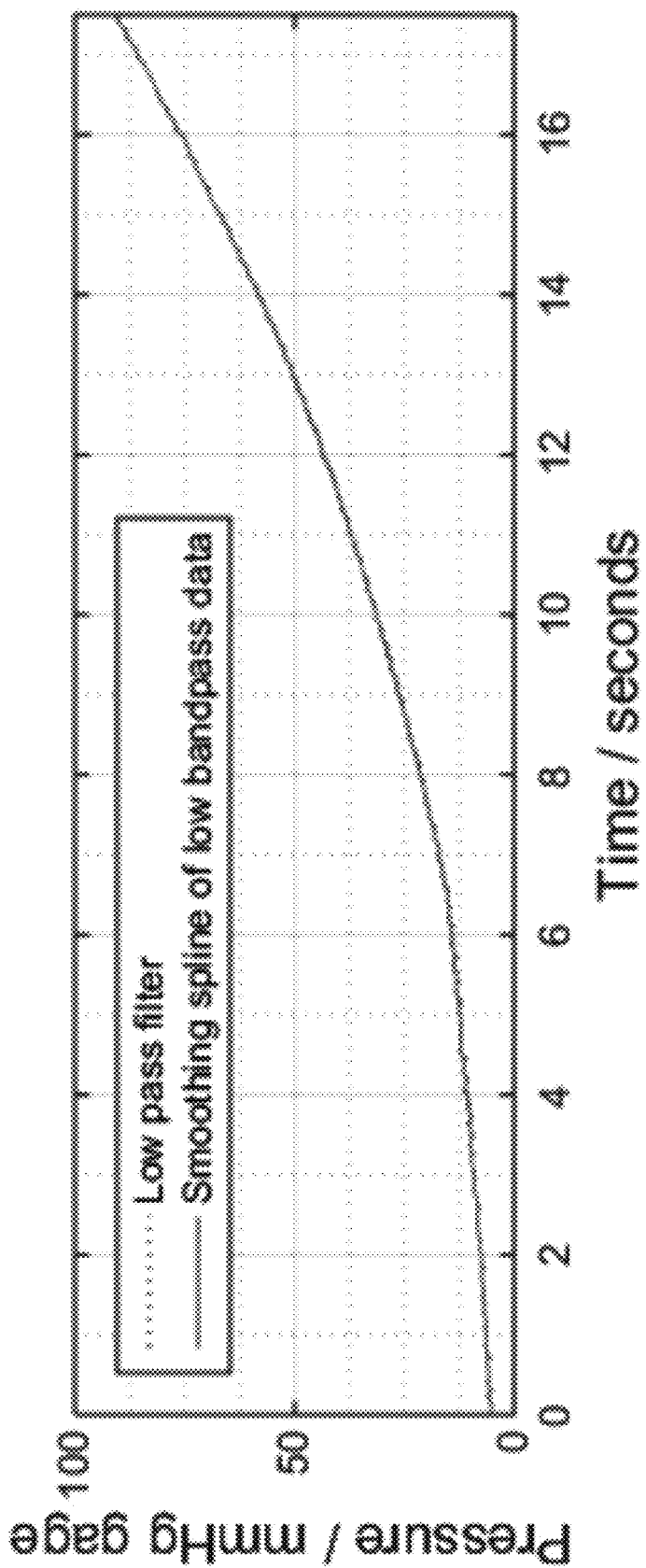

At step 456 the process performs a smoothing operation, for example by calculating a spline smoothing function to match the dataset. This is illustrated in FIG. 10c in relation to the filtered dataset of FIG. 10b. As seen in the graph of 10c, the data points are shown as dots i.e. the low pass filter output. These data points are further smoothed by applying a smoothing spline, as represented by the solid line.

Figure 10D:
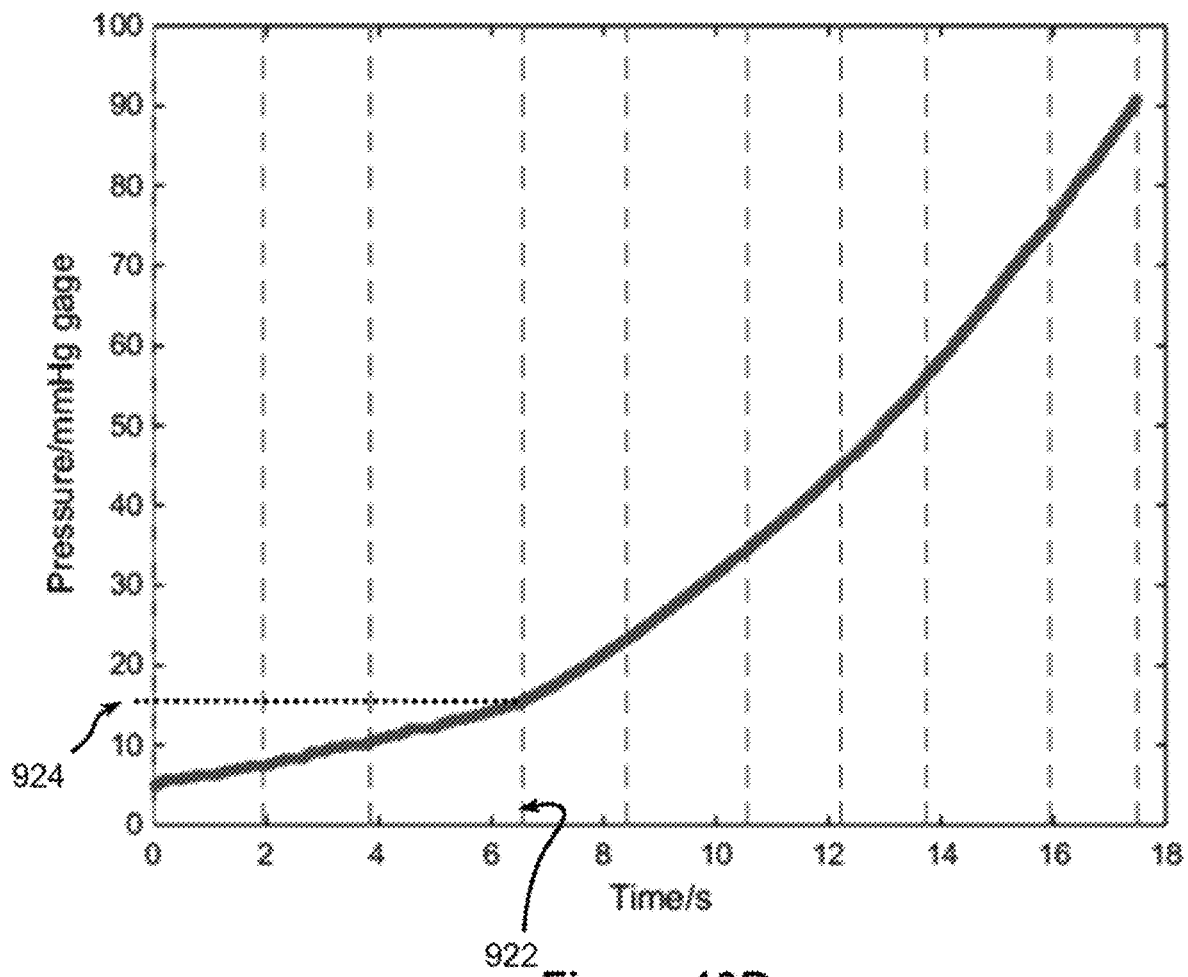

At step 458 the process divides the data curve into sections using "knots", and at step 460 fits a series of linear piecewise functions across the established knots. The knot placement step is illustrated in FIG. 10d. This can use one of many established tools for approximating a given curve with a series of straight lines. The loop of steps 460, 462, 470 and 472 seek to adjust knot placement to optimize the set of linear fits to the smoothed data using a least squares approach, and to fix on a stable determination of a knee pressure. Ultimately this optimization should result in a knot being placed at or close to the knee pressure point, with the data immediately below the knee pressure point having a decidedly lower gradient than the data immediately above the knee pressure point. An example optimized knot sequence is illustrated by the vertical broken lines in FIG. 10d. In this case 10 knots are placed.

Figure 10E:
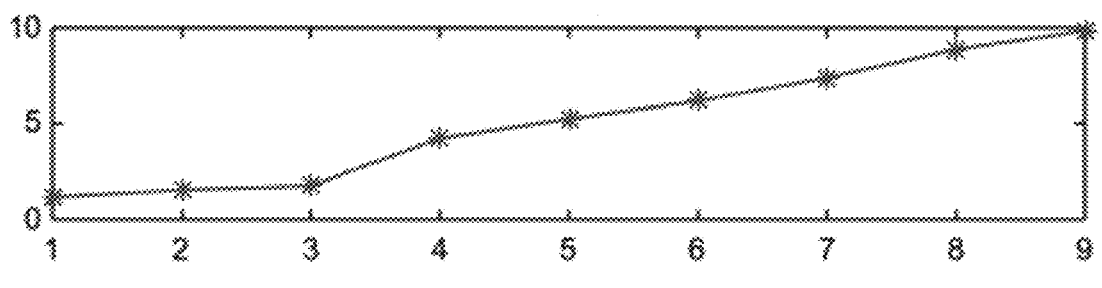
Figure 10F:
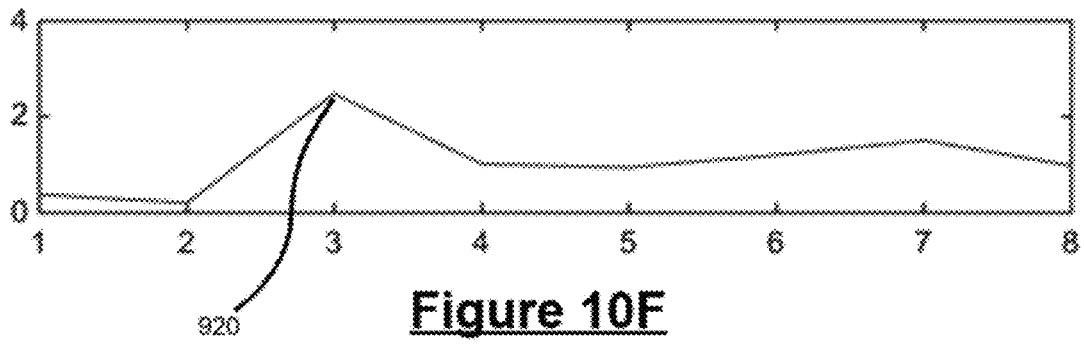

At step 464 the gradients of each of the sequence of linear segments is determined. This data is illustrated in FIG. 10e, for the example data of FIG. 10d. There are 9 data points, relating to the 9 line segments that connected the 10 knots of FIG. 10d. At step 466 the changes in this gradient data are determined. This first derivative of gradient data is illustrated in FIG. 10f. There are 8 data points, indicating the 8 intermediate knots where line segments meet in FIG. 10d. In this data, the knot where the maximum change of gradient occurs is the knot determined to be associated with the pressure knee. In the example data, this is the third data point 920, which represents the third intermediate knot 922 in FIG. 10d, occurring at 6.5 s.

At step 468 the process records the pressure at the determined knot point. In the example dataset this gage pressure is 15 mmHg, as indicated at 924 in FIG. 10d.

Once the loop finds an optimized set of knots with a stable knee pressure at step 472, this knee pressure is stored at step 474 as the determined knee pressure for this calibration event.

Figure 4D:
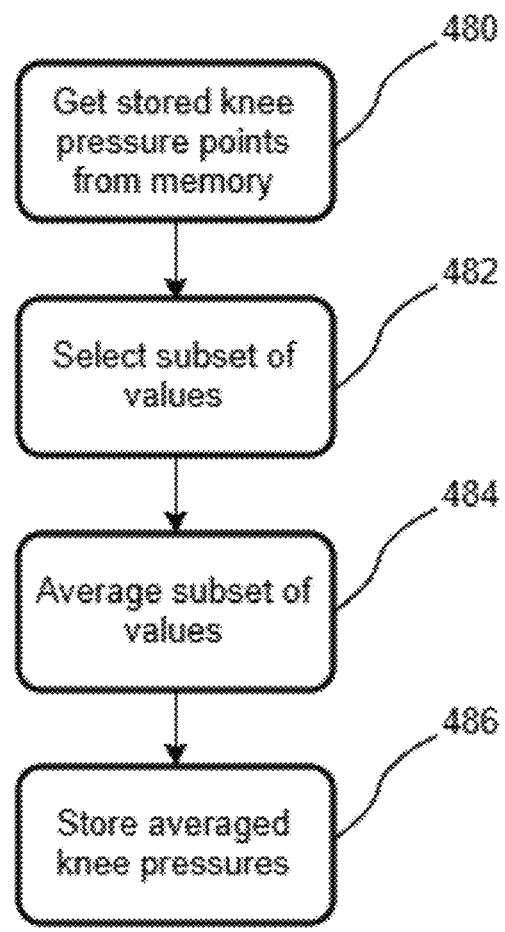

FIG. 4d illustrates in greater detail an example process for improving the reliability of recalibration by removing calibration data that may be assumed to result from a faulty calibration process. The calibration process is susceptible to imperfect technique, with the pressure being raised in a jerky or non-smooth manner. This could result in instances where the process determines the existence of a knee pressure that is not the result of the correct operation of the sensor component.

In the process of FIG. 4d data from a sequence of calibration events is processed to determine an average knee pressure that excludes outliers. At step 480 the process retrieves knee pressure data for a series of calibration events. The number of events in this series is determined by the loop at step 406 of FIG. 4a.

At step 482 the process selects a subset of the values by determining a group of close values, or selecting a set of values that are close to the median value of the data set.

At step 484 the process determines the average value of the subset of the pressure data. The size of this dataset may depend on the size of the dataset. For example, this might be the closest 5 values, or the closest half of the values.

At step 486 this is stored and returned as the averaged knee pressure, which the overall process of FIG. 4a will use to determine whether to set a new zero offset for the sensor, and if so, the value of the zero offset.

This described process is an example only. Wide variation is possible without departing from the intent of the invention, and while retaining one or more aspects of the process including: recognizing valid calibration data; processing data to determine characteristic features that have been deliberately caused to exist at a repeatable pressure through the mechanical design of the sensor housing; checking these determinations for sense by excluding outliers.

Variations on the sensor component are possible which would result in according variations of the process described. For example, the sensor component may be designed such that the diaphragm exhibits multiple distinct changes in effective stiffness, such as by including more than one interfering structure within the cavity, with these structures engaging the diaphragm at different chamber pressures. Alternatively the sensor component may include multiple cavities divided from the chamber by independent diaphragms and interfering structures, each designed to exhibit the characteristic change in stiffness at a different chamber pressure. In this case the process would be modified to determine multiple knee pressures, for example upper and lower knee pressures. This could be achieved for example by determining multiple peaks in the $1^{st}$ derivative of the inter-knot gradient.

In a further variation, the sensor component could include electronic determination of the diaphragm contacting the structure of the cavity, for example by capacitance or conductivity, independently of the pressure sensor. This would allow for more direct recalibration of the sensor at any time that the chamber pressure passes the contact pressure. However, this would preferably operate as an additional recalibration process alongside recalibration using the sensor pressure alone, as the electronic detection of contact could itself be susceptible to drift or other misfunction. In this case, a recalibration process such as defined in FIGS. 4a to 4d could allow for recalibration of the contact pressure of the diaphragm, recalibration of the pressure sensor, or both.

In a further variation, the calibration process including occluding the inlet and outlet tubes may be by means other than pinching a flexible tube, for example by valves. Further, the forced pressure increase by reducing volume may be by other than moving a pinch point on a flexible tube. For example a plunger or other squeezable chamber or sub-chamber may be provided.

In a further variation, the calibration process may include automation. For example pinch valves or other valves may be provided along with electrical actuation, and the pressure increase (volume reduction) may be provided by plunger or cam arrangement, also with electrical actuation.

Figure 2:
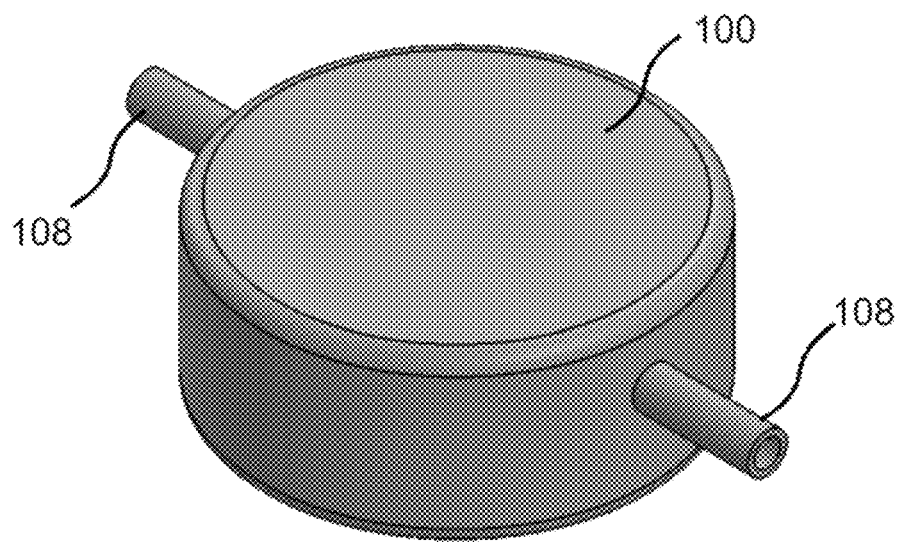
FIG. 2 is a perspective view of the pressure sensor housing of FIG. 1.
Figure 11A:
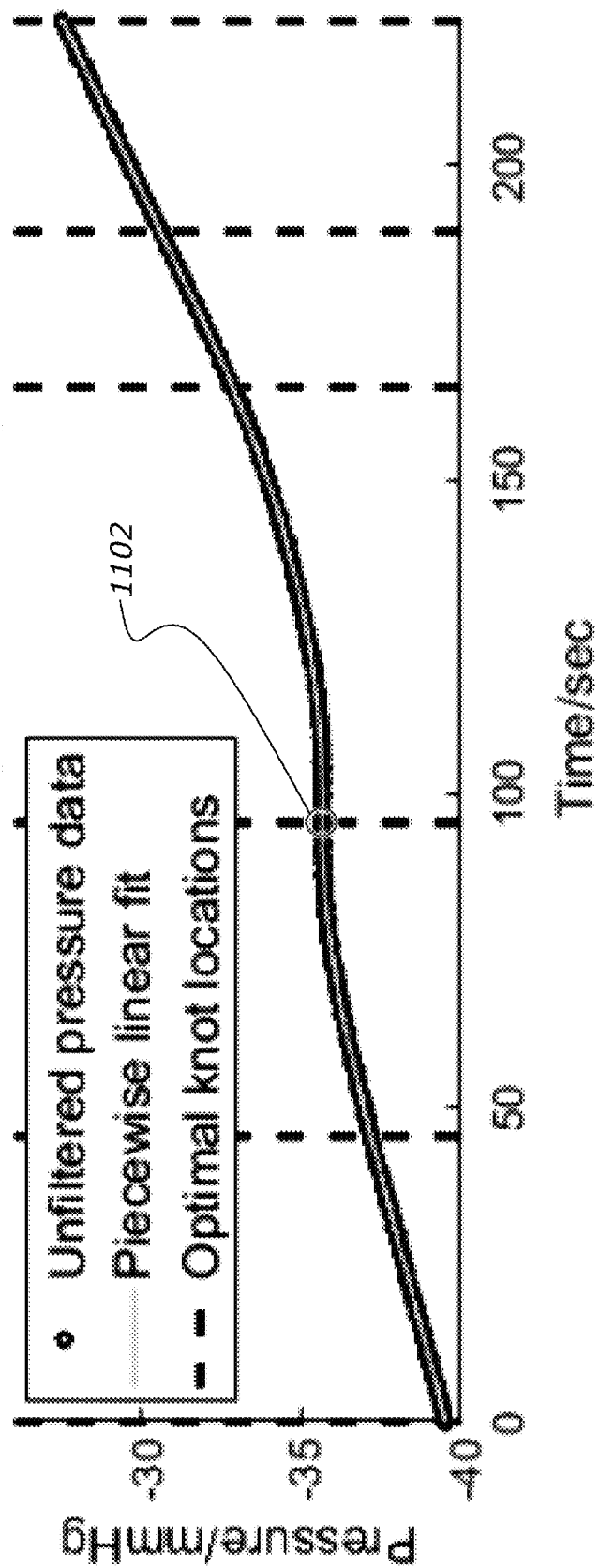
FIG. 11a shows a graph illustrating a knee pressure for a testing protocol on a sensor.
Figure 11B:
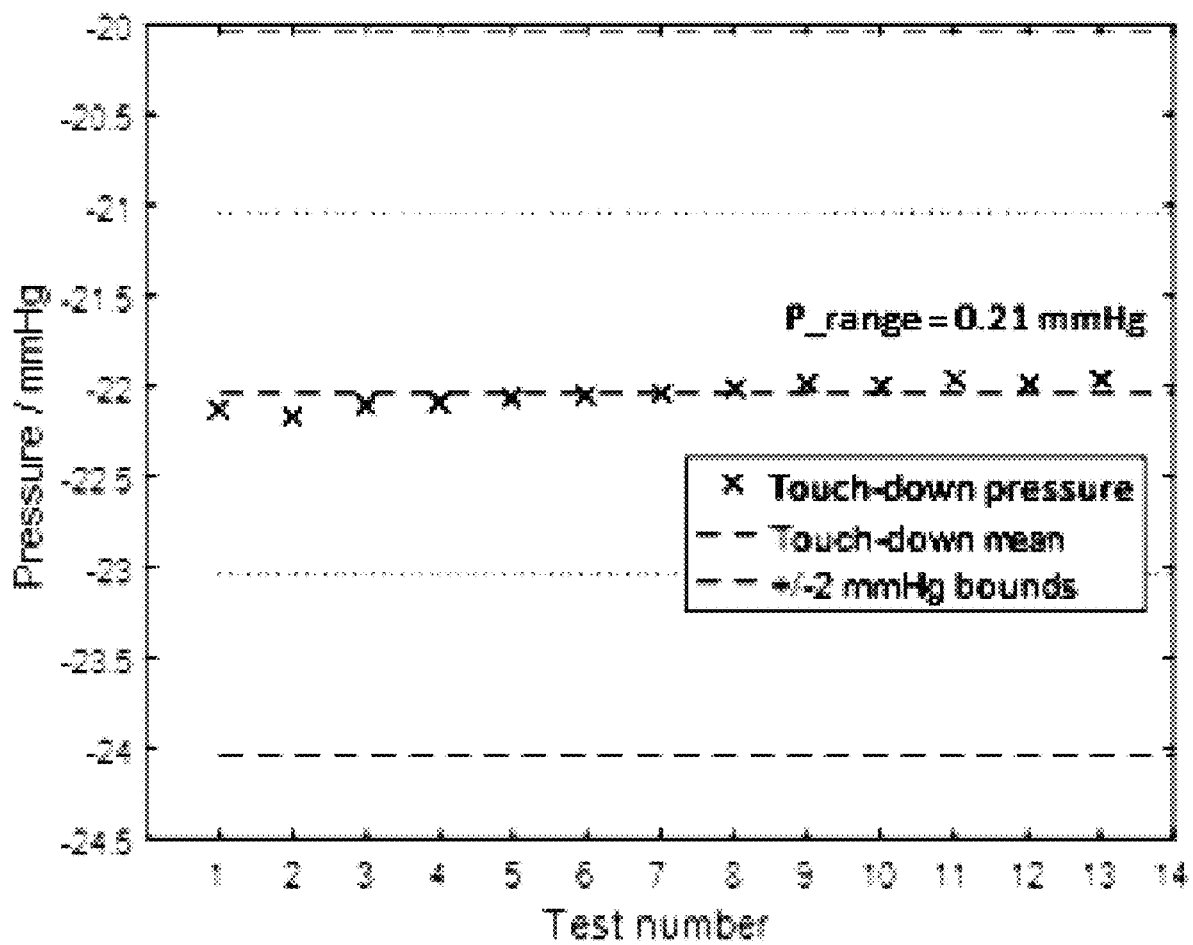
FIG. 11b shows the touch down pressure values over 10 consecutive pressurizations to illustrate repeatability.
Figure 11C:
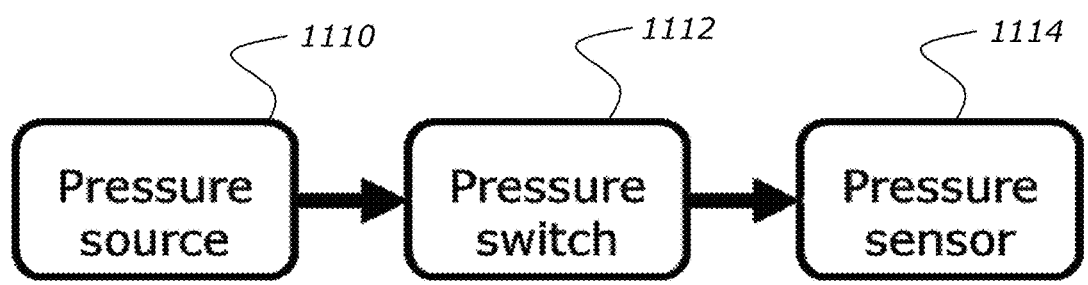
FIG. 11c shows an exemplary experimental set up for executing a testing protocol on the pressure sensor.

Referring now to FIGS. 11a to 11c testing was conducted on a pressure sensor similar to the one described in this specification. The testing comprised of a series of pressurization tests on a sensor having a similar structure to the sensor described herein. The exemplary test sensor apparatus was similar in structure to the sensor described with reference to FIGS. 1 and 2, and also included compliant tubes similar to connected tubes 806 and 808 described with reference to FIG. 8.

Based on the testing results it has been understood that the knee pressure (knee feature) i.e. the point at which there is a discernable discontinuity in the pressure curve. In one testing protocol the input pressure to the pressure sensor was produced using a syringe pump. However, this approach is difficult to replicate outside a laboratory setting. At least one aim of the testing was to try and develop a testing protocol that can be used when the pressure sensor is in situ, i.e. in use and implanted within a user.

A second testing protocol that was used involved pressurization of the pressure sensor by using a person's fingers to depress the connected tubes to the pressure sensor.

The pressure generated by the finger actuation can be regulated using the constricted flow path to reduce the rapid increase in pressure where the finger actuation occurs.

For the finger actuated testing protocol, the characteristic knee pressure can be detected by plotting the pressure values from the pressure sensor. A gradual pressurization without intermittent fluctuation was achieved. The experimental setup shown in FIG. 11c comprises a pressure sensor. In the exemplary test set up 3 pressure sensors were pressurized and simultaneously recalibrated as part of the testing in order to show the recalibration process can be repeated. The recalibration method used was the finger pinching method, as described herein. The testing protocol also comprises detecting the knee pressure over 10 pressurization cycles. FIG. 11c shows an exemplary test set up that was used to test the pressure sensor and show that recalibration can be repeatedly achieved. As seen in FIG. 11c the test set up comprises a pressure source 1110 which may be a syringe or another pressure source. The test set up also includes a pressure switch 1112 and the pressure sensor 1114. The pressure switch 1112 is in fluid communication with the pressure sensor and the pressure source 1110 is in fluid communication with the pressure switch 1112.

FIG. 11a shows the knee pressure that is detected from one sensor over 10 consecutive pressurization cycles. As shown in FIG. 11a there is a discernible knee as indicated by the red circle 1102 at a time of approximately 95 seconds after the pressure calibration test began. As shown in FIG. 11a, the lighter line represents the piecewise linear fit. The dashed lines represent the optimal knot locations i.e. pressure knot locations. The dark line (made of a plurality of dots adjacent each other) are the unfiltered pressure data. The line of best fit passes through a majority of the pressure data to create a best fit line.

FIG. 11b shows the knee pressure points detected from one sensor over 10 consecutive pressurization cycles i.e. the touchdown pressures. The touchdown pressure is the pressure value where the membrane contacts the first upstand. The testing protocol using a regulator provides an improved testing protocol that is repeatable. The testing protocol also shows that the sensor device can be recalibrated to an accuracy of approximately plus or minus approximately 0.1 mmHg. Clinically this is very useful since the finger pinching based recalibration method can be repeatedly used.

Embodiments of the present invention provide for an implantable pressure sensor that can be recalibrated in situ, non-invasively. This extends the useful lifetime of the sensor by allowing compensation for long term drift. The compensation is determined in relation to the performance of a mechanical system which is expected to exhibit minimal drift and variance over time.

While the pressure sensor component, and system, is particularly described in relation to an implantable sensor for use in the medical sphere, it could also be adapted for other applications requiring sensors in locations that are hard to access. A system with automation of the calibration process would be particularly applicable to such an application where necessary miniaturization may prove less challenging.

The invention claimed is:

1. A device comprising:
   a housing enclosing a chamber and having at least one port that communicates with the chamber,
   a pressure sensor receiving fluid pressure from the chamber,
   the chamber having a compliance that exhibits a marked change in volumetric stiffness repeatably at a fixed pressure, wherein the chamber is formed between a first flexible wall portion and a second flexible wall portion, and
   a sealed cavity divided from the chamber by the first flexible wall portion, such that an increasing pressure in the chamber causes increasing deflection of the first flexible wall portion, wherein the pressure sensor is within an enclosure sealed from the chamber by the second flexible wall portion.

2. The device as claimed in claim 1, wherein the sealed cavity or housing is shaped such that as the pressure in the chamber transitions through a first pressure part of the first flexible wall portion transitions from being in contact with a structure of the sealed cavity or housing to being out of contact with the structure.

3. The device as claimed in claim 2, wherein the first flexible wall portion comprises a diaphragm and portions of the diaphragm permit continued deflection at pressures above and below a contact pressure.

4. The device as claimed in claim 3, wherein the first flexible wall portion is out of contact with the structure at pressures below the first pressure, and in contact with the structure at pressures above the first pressure.

5. The device as claimed in claim 2, wherein there is no additional detector for determining contact of the first flexible wall portion with the housing or sealed cavity.

6. The device as claimed in claim 2, wherein portions of the first flexible wall portion permit continued deflection at pressures above and below a contact pressure.

7. The device as claimed in claim 1, wherein the pressure sensor is located in the housing.

8. The device as claimed in claim 1, wherein at least one port includes connection for flexible tubing.

9. The device as claimed in claim 8, wherein the housing includes an inlet port and an outlet port and both inlet and outlet ports include connection for flexible tubing.

10. An assembly comprising a device according to claim 9, wherein a first flexible tube extending from the inlet port and a second flexible tube extending from the outlet port.

11. A hydrocephalus shunt comprising an assembly as claimed in claim 10 and a shunt valve connected with the flexible tube extending from the outlet port.

12. The device as claimed in claim 1, including an interface from the pressure sensor to a controller.

13. The device as claimed in claim 12, including a controller connected to the pressure sensor, an external communications interface connected with the controller and a power supply connected to supply power to the controller.

14. A system including a device as claimed in claim 1, including a processor programmed to process data from the pressure sensor in a calibration method comprising identifying a pressure data point from the pressure sensor that corresponds with a time when the compliance of the chamber changes.

15. The system as claimed in claim 14, wherein the program identifies the time when the compliance of the chamber changes by identifying a knee feature in a pressure data series recorded over the duration of a calibration event.

16. The system as claimed in claim 15, wherein the program identifies a knee feature according to distinct changes in gradient of pressure over time.

17. The system as claimed in claim 14, wherein the program sets a zero offset for use in relation to the pressure sensor based on the recorded output of the pressure at the identified time.

18. The system as claimed in claim 17, wherein the program sets a zero offset for use in relation to the pressure sensor based on the result of multiple instances of the calibration method.

19. The system as claimed in claim 18, wherein the program compares the results of multiple instances of the calibration method and discards at least some of the results in calculating a new zero offset for the pressure sensor.

20. The device as claimed in claim 1, wherein the enclosure is filled with an incompressible liquid.

* * * * *